US00PP09245P

United States Patent [19]

Egger

[11] Patent Number: Plant 9,245

[45] Date of Patent: Aug. 15, 1995

[54] 'LONGIFLORUM×ASIATIC HYBRID LILY PLANT NAMED 'CEB GLOW'

[75] Inventor: Donald L. Egger, Aurora, Oreg.

[73] Assignee: Cebeco Lilies, Inc., Aurora, Oreg.

[21] Appl. No.: 333,257

[22] Filed: Nov. 2, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Klarquist Sparkman Campbell Leigh & Whinston

[57] ABSTRACT

A new and distinct lily hybrid named 'Ceb Glow' characterized by upright, large, vibrant yellow flowers on tall, strong stems excellent for cut flower production.

1 Drawing Sheet

BACKGROUND OF THE INVENTION

The present invention comprises a new and distinct cultivar of lily hybrid, referred to commercially as a *Longiflorum*-Asiatic Lily Hybrid, referred to by the cultivar name 'Ceb Glow'.

This invention is the product of a controlled breeding program in Aurora, Ore. The seed parent was GH-403, a proprietary non-released plant. The pollen parent was AM #2, another proprietary non-released plant.

The *longiflorum*-Asiatic cross is relatively new to the trade. This type of cross was originally made to create colored *Lilium longiflorum* hybrids. Instead, due to the difficulty in crossing back to *L. longiflorum,* the plants that were developed had to be crossed with Asiatic lilies. As such, the results look more like Asiatic lilies. The resulting hybrids often have several advantages, not necessarily in combination, over an Asiatic lily: (1) often larger flowers; (2) often larger, waxier leaves; (3) hybrid vigor; (4) lower susceptibility to scorch; (5) excellent flower texture and substance; (6) more virus resistance; (7) new and clearer colors; and (8) stronger, sturdier stems.

This invention has not been observed under all possible environmental conditions. The phenotype may vary significantly with variations in environment such as temperature, light intensity, and day length, without, however, any variation in genotype. The following traits have been repeatedly observed in asexually propagated progeny and are determined to be the basic characteristics of this invention which in combination distinguish this lily as a new and distinct cultivar: (1) large, upright vibrant yellow flowers with a white eye and some maroon spots; (2) large yellow buds; (3) tall, strong stems for cut flowers; (4) excellent vase life and (5) good vigor. Bulbs of this plant may be precooled and forced out of season for very uniform cut flower production.

To the inventor's knowledge, there are no other *longiflorum*-Asiatic lily hybrids with this color flower suitable for cut flower forcing on the market. Compared to my other new variety, 'Ceb Sun', 'Ceb Glow' has shorter stems, narrower tepals, smaller more numerous leaves, smaller buds and flowers, and an earlier bloom time.

Asexual reproduction of this new variety has been initially and subsequently accomplished at Cebeco Lilies, Inc. in Aurora, Ore., by scaling and tissue culture. The resulting plants have shown that the above-mentioned unique features are stable and reproduce true to type in each successive propagation.

Figure 2:
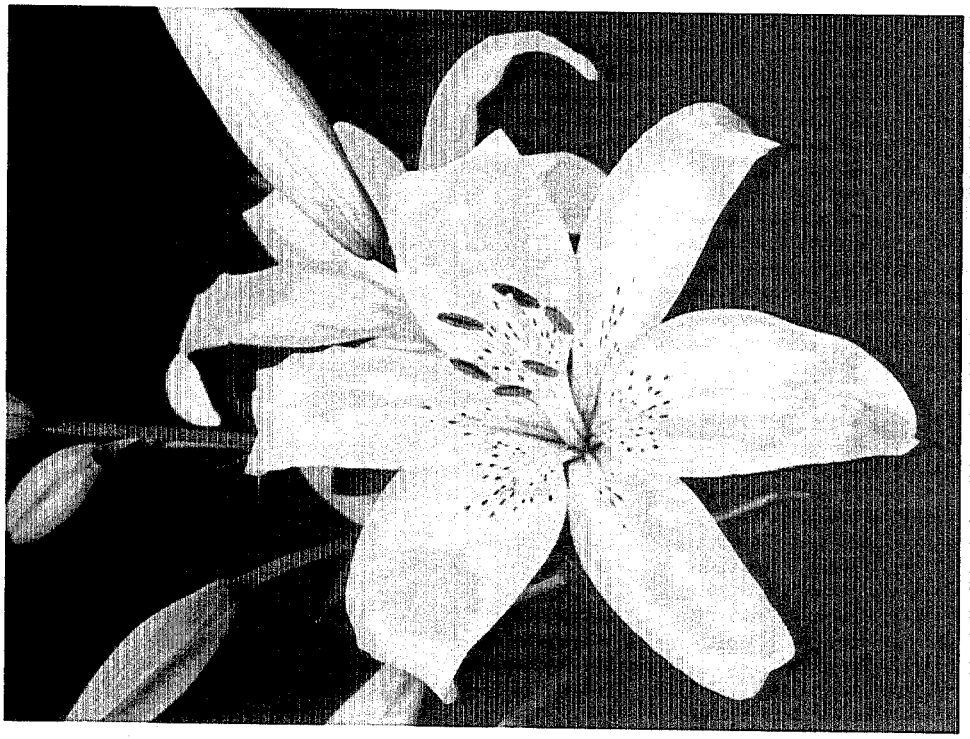
FIG. 2 is a close-up photograph which illustrates in greater detail a single flower of the new plant.
Figure 1:
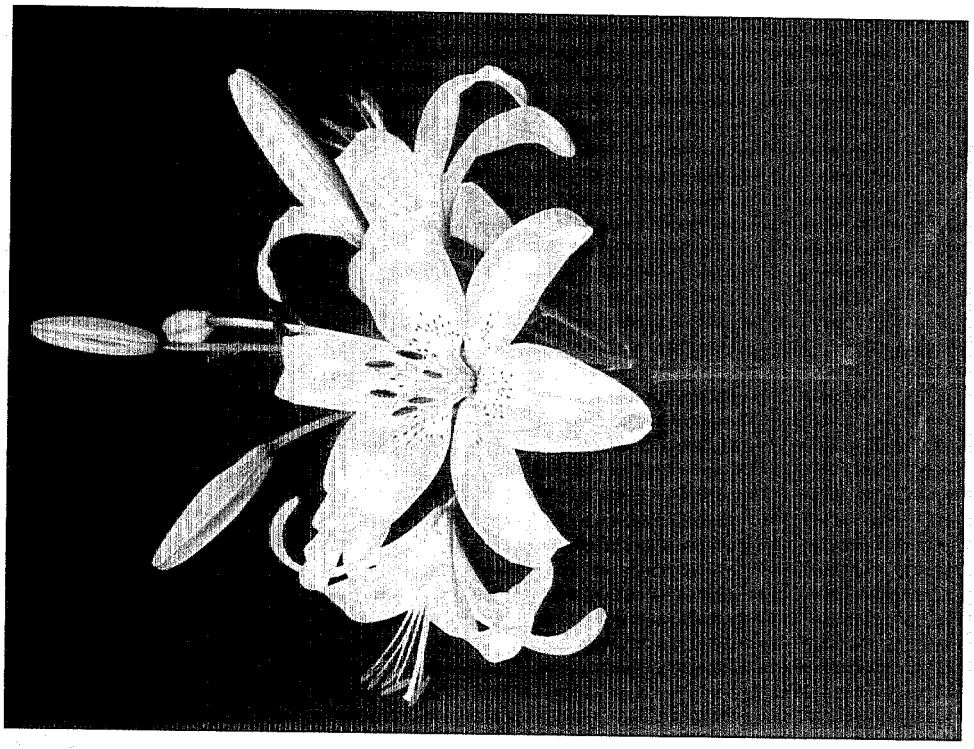
FIG. 1 is a photograph showing the 'Ceb Glow' lily.

The photographs of the drawing were taken in August 1993 in a studio and illustrates the typical flower and foliage form, with color being as true as is reasonably possible in this type of color photograph.

DETAILED DESCRIPTION

The following is a detailed description of the invention based on plants produced under commercial practices in the Cebeco Lilies, Inc. greenhouses in Aurora, Ore. in July 1993. Color references are made to The Royal Horticultural Society Colour Chart (R.H.S.), except where the context indicates a term having its ordinary dictionary meaning.

THE PLANT

Origin: Seedling.

Parentage:

*Seed parent.*—GH-403.

Pollen parent.—AM #2.

Commercial classification: Upright *longiflorum*-Asiatic hybrid, cut flower type.

Classification: Division VIII, according to the Horticultural Classification of Lilies by The Royal Horticultural Society of London.

Form: Single erect stem bearing terminal cluster of flowers.

Height: About 65–85 cm. from the top of the soil to the top of the flowers from bulbs of 12–14 cm. in circumference.

Growth habit: Vigorous, upright and rigid.

Foliage:

*Arrangement.*—Spiral.

*Quantity.*—Average.

*Leaf size.*—Variable, from about 7.4–12.2 cm. long and about 1.6–2.1 cm. wide.

*Leaf shape.*—Lanceolate.

*Texture.*—Leathery.

*Aspect.*—Glossy.

*Color.*—Medium green on both sides, closest to b 147A.

Bulbs:

*Size.*—Variable, ranging to about 12–14 cm. in circumference as used commercially.

*Color.*—White.

THE BUD

Size: To about 9.5 cm. long and 3 cm. wide just prior to opening.

Shape: Narrow ovoid. The bud is at a slight tilt relative to the pedicel until mature.

Rate of opening: The mature bud opens slowly in response to light.

Color: Greenish yellow. Green-Yellow Group 1B with more yellow green at the tip.

THE FLOWER

Blooming habit: Annually, once and early season.

Days to bloom: Flowers approximately 76 days after spring greenhouse planting under typical commercial flower forcing conditions of 15° Celsius night time temperatures.

Flower size: Large.

*Diameter.*—About 19 cm.

*Depth.*—About 5–6 cm.

Borne: In an umbel or modified raceme of 3–7 flowers from bulbs 12–14 cm. in circumference. On a larger bulb of 16 cm. the raceme has 15 flowers.

Shape: When the flower first opens it is bowl-shaped. Later, the shape flattens out and the tepals reflex slightly at the tips.

Tepalage:

*Number.*'Six.

*Arrangement.*—Imbricated.

*Shape.*—Ovate.

*Texture.*—Leathery, spongy.

*Aspect.*—Satiny.

*Size.*—Length: About 10.5 cm. Width: Inner tepals — about 5.7 cm. Outer tepals — about 4.2 cm. Depth of imbrication: About 12 mm.

*Nectary.*—About 3.5 cm. long; yellow green; pubescent; with the channels together.

*Projections.*—Few, inconspicuous.

*Spots.*—Maroon, Grayed-Purple Group 187B; above the nectary; about 10 to 30 per tepal, linear.

*Blush.*—Light yellow, Yellow Group 9D; located around the nectary.

*Color.*—Topside: Yellow. Yellow Group 9A. Topside base: Light yellow. Yellow Group 9D. Bottomside: Yellow. Yellow Group 9A. Bottomside base: Light Yellow. Yellow Group 9D.

*Discoloration.*—Slight with age.

*Fragrance.*—Slight.

*Lasting quality.*—Excellent.

Pedicel:

*Length.*—Long. Varies from about 9–16 cm.

*Color.*—Yellow-green.

*Orientation.*—Ascending upwardly from about 30°–45° from the horizontal.

THE REPRODUCTIVE ORGANS

Stamens:

*Number.*—Six, typical of the genus Lilium.

*Anthers before dehiscence.*—Size: About 2.3 cm. Color: Light brown. Grayed-Orange Group 177A-B.

*Filaments.*—Length: About 78 mm. Color: Greenish yellow. Green-Yellow Group IC-D.

*Pollen.*Color: Orange. Grayed-Orange Group 165B.

Pistil:

Number.—One.

*Style.*—Length: About 70 mm. Color: Green-Yellow Group 1A to 1D at the base.

*Stigma.—Color: Yellow, Yellow Group* 4B.

THE FRUIT

Fertility: The fruit is of low fertility.

Shape: Ovoid.

Color at maturity: Soft Brown.

I claim:

1. A new and distinct cultivar of *longiflorum*-Asiatic hybrid lily plant substantially as herein shown and described.

* * * * *